United States Patent [19]

Louthan

[11] 4,307,225

[45] Dec. 22, 1981

[54] PREPARATION OF ALKYL MERCAPTOCARBOXYLATE/DIALKYL THIODICARBOXYLATE MIXTURE USING SULFUR AND/OR WATER COCATALYST

[75] Inventor: Rector P. Louthan, Bartlesville, Okla.

[73] Assignee: Phillips Petroleum Company, Bartlesville, Okla.

[21] Appl. No.: 157,583

[22] Filed: Jun. 9, 1980

Related U.S. Application Data

[60] Division of Ser. No. 966,718, Dec. 5, 1978, Pat. No. 4,232,167, which is a continuation of Ser. No. 737,949, Nov. 2, 1976, abandoned, which is a continuation-in-part of Ser. No. 720,475, Sep. 3, 1976, abandoned.

[51] Int. Cl.$^3$ .................... C08G 63/04; C08G 63/34
[52] U.S. Cl. ............................... 528/279; 528/274; 528/293; 528/297; 528/300; 560/154
[58] Field of Search ............... 528/274, 279, 293, 297, 528/300; 560/154

[56] References Cited

U.S. PATENT DOCUMENTS

| | | | |
|---|---|---|---|
| 4,052,440 | 10/1977 | Gladstone et al. | 560/154 |
| 4,113,707 | 9/1978 | Louthan et al. | 528/279 |
| 4,232,167 | 11/1980 | Louthan | 560/154 |

*Primary Examiner*—Lucille M. Phynes

[57] ABSTRACT

An olefinically unsaturated alkyl carboxylate is reacted with hydrogen sulfide in the presence of a lower alkanol using an addition catalyst with water and/or sulfur cocatalyst to give an alkyl mercaptocarboxylate/dialkyl thiodicarboxylate mixture having a high proportion of the mercaptocarboxylate. If sulfur is contained in the cocatalyst, dialkyl dithiodicarboxylates are also formed. The resulting mixture on transesterification with a poly(oxyalkylene)-polyol gives a poly(oxyalkylene)-polyester-poly(monosulfide)-polythiol or a poly(oxyalkylene)-polyester-poly(monosulfide)-poly(disulfide)-polythiol having a good balance of properties.

19 Claims, No Drawings

PREPARATION OF ALKYL MERCAPTOCARBOXYLATE/DIALKYL THIODICARBOXYLATE MIXTURE USING SULFUR AND/OR WATER COCATALYST

CROSS REFERENCE TO RELATED APPLICATIONS

This is a division of copending application Ser. No. 966,718, filed Dec. 5, 1978, now U.S. Pat. No. 4,232,167, which is a continuation of application Ser. No. 737,949, filed Nov. 2, 1976, which in turn is a continuation-in-part of application Ser. No. 720,475, filed Sept. 3, 1976, both now abandoned.

BACKGROUND OF THE INVENTION

This invention relates to the production of alkyl mercaptocarboxylate/dialkyl thiodicarboxylate mixtures, or alkyl mercaptocarboxylate/dialkyl thiodicarboxylate/dialkyl dithiodicarboxylate mixtures. The production of mercapto derivatives of unsaturated esters as a transitory intermediate in the production of thiodiesters is broadly known as disclosed in U.S. Pat. No. 2,845,390. It has been found that polymers suitable for sealants can be prepared by transesterification using a mixture of alkyl mercaptocarboxylates and dialkyl thiocarboxylates with a poly(oxyalkylene)-polyol. However, the resulting product, on curing, is too brittle if the mixture contains too much of the dialkyl thiodicarboxylate.

SUMMARY OF THE INVENTION

It is an object of this invention to provide a method of making mixed esters for ester interchange to produce poly(oxyalkylene)-polyester-poly(monosulfide)-polythiols or poly(oxyalkylene)-polyester-poly(monosulfide)-poly(disulfide)-polythiols;

it is a further object of this invention to provide a poly(oxyalkylene)-polyester-poly(monosulfide)-poly(disulfide)-polythiol having good storage stability;

it is a further object of this invention to provide a simplified method of producing poly(oxyalkylene)-polyester-poly(monosulfide)-polythiols or poly(oxyalkylene)-polyester-poly(monosulfide)-poly(disulfide)-polythiols;

it is a further object of this invention to provide poly(oxyalkylene)-polyester-poly(monosulfide)-poly(disulfide)-polythiols having a good balance of physical properties; and it is a further object of this invention to provide a poly(oxyalkylene)-polyester-poly(monosulfide)-poly(disulfide)-polythiol having an acid number of less than 0.01, preferably 0.00.

In accordance with this invention, an olefinically unsaturated carboxylate is reacted with hydrogen sulfide using an addition catalyst in the presence of a lower alcohol with sulfur and/or water as a cocatalyst.

DESCRIPTION OF THE PREFERRED EMBODIMENTS

This invention pertains to the preparation of mixed esters suitable for transesterification to produce a poly(oxyalkylene)-polyester-poly(monosulfide)-polythiol or a poly(oxyalkylene)-polyester-poly(monosulfide)-poly(disulfide)-polythiol having more than two pendant thiol groups per molecule. The resulting polymers are liquid at room temperature and generally have a viscosity at 25° C. within the range of 3,000 to 10,000, preferably 5,000 to 8,000 centipoises.

Hydrogen sulfide is reacted in the presence of a lower alcohol with at least one olefinically unsaturated alkyl carboxylate using an addition catalyst and a cocatalyst selected from sulfur and/or water to give a mixture of at least one alkyl mercaptocarboxylate and at least one dialkyl thiodicarboxylate (if sulfur is included in the cocatalyst, which is preferred, at least one dialkyl dithiodicarboxylate is also produced) which mixture is then transesterified in the presence of a transesterification catalyst with a poly(oxyalkylene)-polyol having more than two hydroxy groups per molecule to give a poly(oxyalkylene)-polyester-poly(monosulfide)-polythiol or a poly(oxyalkylene)-polyester-poly(monosulfide)-poly(disulfide)-polythiol. The cocatalysts greatly increase the proportion of alkyl mercaptocarboxylate to dialkyl thiodicarboxylate. In the absence of sulfur and water, the desired high proportion of the alkyl mercaptocarboxylate is not formed even in the presence of a substantial excess of hydrogen sulfide, although varying the ratio of hydrogen sulfide in the reaction does give some change in the proportion of alkyl mercaptocarboxylate formed. Thus, by using sulfur and/or water to substantially increase the amount of alkyl mercaptocarboxylate formed and then varying the amount of hydrogen sulfide used, the reaction can be fine tuned to give the exact proportion desired. This makes possible the use of the reaction mixture of esters directly with a poly(oxyalkylene)-polyol to give a polymer having a good balance of properties since the polymer tends to be too soft if not enough alkyl mercaptocarboxylate is used. The use of the cocatalyst results in an ester mixture which is approximately optimum for giving a good polymer. The ratio of hydrogen sulfide to unsaturated carboxylate can be adjusted to give exactly the right ratio of esters since too much alkyl mercaptocarboxylate causes the resulting polymer to be too brittle.

If sulfur is used as the cocatalyst or a part of the cocatalyst, a small amount of dialkyl dithiodicarboxylate is also produced as noted above to give, on reaction with the polyol, poly(oxyalkylene)-polyester-poly(monosulfide)-poly(disulfide)-polythiol. A very small amount of dialkyl polythiocarboxylate, i.e., with more than two sulfur atoms, may also be formed.

The poly(oxyalkylene)-polyester-poly(monosulfide)-polythiol or poly(oxyalkylene)-polyester-poly(monosulfide)-poly(disulfide)-polythiol produced from the mixed esters of this invention is readily oxidatively coupled or cured in an appropriate formulation to form a cured or coupled composition which is useful, e.g., as a sealant. The sealant comprises the poly(oxyalkylene)-polyester-poly(monosulfide)-polythiol or poly(oxyalkylene)-polyester-poly(monosulfide)-poly(disulfide)-polythiol, a filler and a curing agent. The filler generally comprises an inert inorganic filler and a pigment, either inorganic or organic. Other materials may be present such as cure modifiers, plasticizers, extenders, stabilizers, modifiers, adhesion promoters, and the like. Generally, the sealant will contain 10 to 99, preferably 30 to 75 percent of weight of the poly(oxyalkylene)-polyester-poly(monosulfide)-polythiol or poly(oxyalkylene)-polyester-poly(monosulfide)-poly(disulfide)-polythiol and the remainder nonelastomer ingredients as set out hereinabove.

The poly(oxyalkylene)-polyester-poly(monosulfide)-polythiols or poly(oxyalkylene)-polyester-poly(monosulfide)-poly(disulfide)-polythiols can be cured in a sealant formulation with conventional curing agents including free oxygen-containing fluids such as, for example, air; organic peroxide and hydroperoxides such as, for example, di-tert-butyl peroxide and cumene hydroperoxide; metal oxides such as, for example, the oxides of lead, zinc, manganese, calcium, barium, copper, mercury, tin and iron; metal salts of carboxylic acids such as, for example, lead stearate, zinc laurate, zinc acetate; ammonium persulfate; sulfur; and the like. The curing time will vary with the polymer, the curing agent, the sealant formulation, and the temperature. In general, sufficient curing agent is employed to convert at least about 70 percent of the pendant thiol groups to polysulfide groups.

The olefinically unsaturated alkyl carboxylates useful in this invention are those of formula I $$CR_2=CR-(CR_2)_n-CO_2R' \quad (I)$$

wherein R' is an alkyl radical containing from 1 to 5 carbon atoms, wherein R is hydrogen or R', wherein n is zero or an integer having the value of 1, 2 or 3 and wherein the total number of carbon atoms in all of the R and R' groups is 1 to 15 carbon atoms per molecule.

Specific examples of useful compounds of formula I include methyl acrylate, ethyl acrylate, methyl methacrylate, ethyl 3-butenoate, n-butyl 5-hexenoate, isopropyl 5-undecenoate, n-pentyl 2-(2,2-dimethylpropyl)-5-undecenoate, t-butyl 2-methyl-2-heptenoate, methyl 3,3-dimethyl-5-hexenoate, n-propyl 2,2,3,3,4,4,5-heptamethyl-5-heptenoate and the like.

Useful addition catalysts include well-known organic and inorganic bases such as sodium hydroxide, potassium hydroxide, sodium methoxide, ammonia, ammonium hydroxide, dimethylamine, triethylamine, N,N-diethylaniline, pyridine, 3-ethyl-4-methylpyridine and the like. Ammonium hydroxide is presently preferred.

The addition of hydrogen sulfide to the olefinically unsaturated alkyl ester can be carried out in the presence or absence of diluents in addition to the lower alcohol. It is possible to employ diluents consisting of: saturated aliphatic, saturated cycloaliphatic or aromatic hydrocarbons containing 5 to 8 carbon atoms; or cyclic or acyclic ethers containing from 4 to 8 carbon atoms. Exemplary diluents include pentane, hexane, isooctane, cyclohexane, benzene, toluene, the xylenes, diethyl ether, di-n-butyl ether, tetrahydrofuran and p-dioxane.

The addition of hydrogen sulfide to the olefinically unsaturated alkyl ester is conducted under whatever conditions of temperature, pressure and time are desirable to achieve the desired results. Temperatures in the range of 25° C. to 150° C. are generally useful for the reaction; however, due to the frequently exothermic nature of the reaction, it may be desirable to provide external cooling capability to the reactor. Pressures which are useful in this reaction are generally in the range of 200 psig to 2000 psig (1350 to 13,500 kPa) and preferably in the range of 200 psig to 500 psig (1350 to 3450 kPa). Reaction times of 1 minute to 24 hours are generally useful, but a period of 30 minutes to 5 hours is preferable.

Hydrogen sulfide and olefinically unsaturated alkyl esters are generally employed in amounts ranging from 0.5 to 10 moles hydrogen sulfide per mole of unsaturated ester and preferably in amounts ranging from 1 to 3 moles H₂S per mole of ester.

Any amount of diluent may be employed in the addition reaction which produces the desired results. It is preferable to use 0.3 to 1 part by weight diluent per part by weight unsaturated ester.

Effective amounts of catalyst are usually in the range of 0.0001 to 0.1 part by weight catalyst per part by weight unsaturated ester, but any effective amount can be used. A preferred range of catalyst amount is 0.001 to 0.05 part by weight catalyst per part by weight unsaturated ester.

The lower alcohol is used in an amount within the range of 0.02 to 4 parts by weight per part by weight of unsaturated ester, preferably 0.04 to 0.4 parts by weight per part by weight of unsaturated ester. More can be used if desired as an excess has no particular detrimental effect so long as at least 0.02 part by weight is used. By lower alcohol is meant 1 to 5 carbon atom alcohols such as methanol, ethanol, and isopropanol. Methanol is currently preferred.

Sulfur is employed in the addition reaction in amounts ranging from 0.0001 to 0.2 part by weight sulfur per part by weight unsaturated ester and preferably in the range of 0.002 to 0.05 part sulfur per part ester. Water is employed in an amount within the range of 0.0001 to 0.2, preferably 0.004 to 0.1, parts by weight per part by weight of ester. The sulfur or water can be employed alone or both can be employed. The water can come from the water in the catalyst if, for instance, concentrated ammonium hydroxide is used. If it is desired to have no water, anhydrous ammonia, for instance, can be used. Or, water can be added in the exact amount desired.

Following the addition of the hydrogen sulfide to the olefinically unsaturated alkyl ester it is desirable to remove the volatile diluent, unreacted starting materials and volatile by-products. This is readily accomplished by flashing the undesired volatile components of the reaction mixture. The resulting residue, a mixture containing predominantly alkyl mercaptocarboxylate and dialkyl thiodicarboxylate with a small portion of dialkyl dithiodicarboxylate (if sulfur is the cocatalyst) is then used directly for the transesterification reaction.

While it is a purpose of this invention to provide an addition reaction product containing the desired proportion of alkyl mercaptocarboxylate to dialkyl thiodicarboxylate for use directly in the transesterification reaction, it is also within the scope of the invention to separate, for instance by fractional distillation of the crude reaction mixture to obtain a fraction enriched in alkyl mercaptocarboxylate and a fraction enriched in dialkyl thiodicarboxylates. Appropriate amounts of the resulting fractions are then combined to provide a mixture containing precisely the desired proportion of alkyl mercaptocarboxylate, dialkyl thiodicarboxylate and dialkyl dithiodicarboxylate, if any, for the subsequent transesterification reaction.

Alkyl mercaptocarboxylates which are produced by the process of this invention are represented by formula II:

$$HS-(CR_2)_p-COOR' \quad (II)$$

wherein R and R' are as described above, wherein p is an integer having a value of from 2 to 5, and wherein formula II contains 1 to 15 carbon atoms in all R and R' groups per molecule.

Examples of such alkyl mercaptocarboxylates include methyl 2-mercaptopropionate, methyl 3-mercaptopropionate, ethyl 4-mercaptobutyrate, n-butyl 6-mercaptohexanoate, isopropyl 6-mercaptoundecanoate, n-pentyl 6-mercapto-2-(2,2-dimethylpropyl)undecanoate, t-butyl 2-mercapto-2-methylheptanoate, methyl 3,3-dimethyl-6-mercaptohexanoate, n-propyl 6-mercapto-2,2,3,3,4,4,5,5,6-nonamethylheptanoate and the like.

Dialkyl thiodicarboxylates which are produced by the process of this invention are represented by formula III:

$$R'OOC\text{-}(CH_2)_p\text{-}S\text{-}(CR_2)_p\text{-}COOR' \qquad (III)$$

wherein R, R' and p are as defined above; with a total of 2 to 30 carbon atoms in all R and R' groups per molecule.

Also produced, if sulfur is included in the cocatalyst, is about 0.5 to 20, preferably 1 to 10, weight percent based on the total weight of the mixed esters of the polysulfide of formula IV:

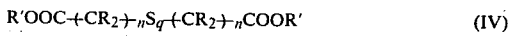

$$R'OOC\text{-}(CR_2)_n\text{-}S_q\text{-}(CR_2)_n\text{-}COOR' \qquad (IV)$$

wherein R, R' and n are as above and q is an integer of 2 to 5, preferably 2.

Specific examples of dialkyl thiodicarboxylates produced include dimethyl 3,3'-thiodipropionate, diethyl 4,4'-thiodibutyrate, di-n-butyl 6,6'-thiodihexanoate, diisopropyl 6,6'-thiodiundecanoate, di-n-pentyl 6,6'-thiobis [2-(2,2-dimethylpropyl)undecanoate], di-t-butyl 2,2'-thiobis(2-methylheptanoate), dimethyl 6,6'-thiobis(3,3-dimethylhexanoate), di-n-propyl 6,6'-thiobis(2,2,3,3,4,4,5,5,6-nonamethylheptanoate), dimethyl ester of 3-[(carboxymethyl)thio]propionic acid, and the like. The dialkyl polythiodicarboxylates are those corresponding to the above monothiodicarboxylates, i.e., dimethyl 3,3'-dithiodipropionate, etc.

The poly(oxyalkylene)-polyols or polyhydroxy polyethers employed to make the polymer have on average more than two and generally at least on the average 2.5, preferably at least three, pendant hydroxy groups per molecule. Such polyhydroxy polyethers or poly(oxyalkylene)-polyols have more than two, preferably three to about twelve, hydroxyl groups per molecule and molecular weights of from about 200 to about 20,000. These materials can be produced by the reaction of one or more epoxy-substituted hydrocarbons of the general formulas V and VI:

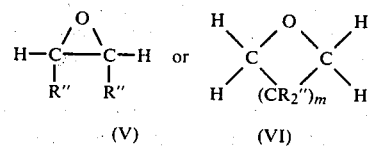

(V)   (VI)

with a polyol of the general formula VII:

$$Y(OH)_x \qquad (VII)$$

wherein R'' can be H or alkyl with the total number of carbon atoms in the molecule being in the range of up to and including about 20; and wherein m is an integer of from 1 to about 10, preferably 1 to 3; and wherein Y is a hydrocarbon moiety with at least two and ordinarily from 3 to 40 carbon atoms per moiety and a valence equal to the value of x, x being an integer of at least two and ordinarily from 3 to about 20, and the number of carbon atoms per molecule of $Y(OH)_x$ is equal to or greater than x.

Polyols that are employed in the preparation of the poly(oxyalkylene)-polyols or polyhydroxy polyethers comprise hydroxy-substituted hydrocarbons that are preferably saturated aliphatics, saturated cycloaliphatics, aryls, or combinations thereof that are substituted with more than two and preferably at least three hydroxyl groups per molecule. In the presently preferred embodiment of this invention, these polyols $Y(OH)_x$, can have from two up to about 12 hydroxyl groups per molecule, and can contain from 3 to about 20 carbon atoms per molecule. Illustrative of the polyols useful in this invention that can be represented by the general formula $Y(OH)_x$ are ethylene glycol, 1,3-propanediol, 2-butene-1,4-diol, 1,4-cyclohexanediol, 2-ethylhexane-1,3-diol, glycerine, pentaerythritol, erythritol, 1,3,8-trihydroxycyclododecane, estriol, 1,4,5,8-naphthalenetetrol, di(p-hydroxyphenyl) phenyl methanol, 1,2,6-hexanetriol, 1,2,4,6,7,9,12,14,15,17,19,20-cicosanedodecol, and the like.

The poly(oxyalkylene)-polyols or polyhydroxy polyethers can be prepared by contacting at least one polyol of the formula $Y(OH)_x$, as defined above, with an epoxy-substituted hydrocarbon, as defined above, under suitable polymerization conditions, as is known in the art. For instance, glycerine can be contacted with an excess of propylene oxide (1,2-epoxypropane) under elevated pressure and in the presence of suitable polymerization promoters. Products of this type can also be obtained from commercial sources. Niax Polyol LHT-67 (a trademark) is a commercial product of this type. In the preparation of poly(oxyalkylene)-polyols having on average more than two pendant hydroxyl groups per molecule, mixtures of the above polyols such as at least one diol and another polyol can be reacted with the epoxy-substituted hydrocarbons defined above to form poly(oxyalkylene)-polyols having more than two pendant hydroxy groups on average per molecule. For instance, a mixture of 1,4-butanediol and 1,2,6-hexanetriol can be reacted with ethylene oxide to produce a poly(oxyethylene)-polyol having an average of more than two pendant hydroxy groups per molecule. Alternatively, a poly(oxyalkylene)-polyol produced, e.g., by the reaction of a diol such as ethylene glycol with an alkylene oxide such as propylene oxide, can be mixed with another poly(oxyalkylene)-polyol produced, e.g., by the reaction of a triol such as 1,2,6-hexanetriol with an alkylene oxide such as propylene oxide. As yet another alternative, up to about 30 weight percent of the poly(oxyalkylene)-polyol can be replaced with a polyol having recurring ester linkages e.g., an average of about 2 to about 5 ester linkages per molecule, in place of at least a portion of the ether linkages produced, e.g, by reaction of a lactone such as caprolactone with a polyol such as ethylene glycol or with an alkylene oxide-polyol condensation product such as diethylene glycol.

Illustrative examples of the epoxy-substituted hydrocarbons of the above-defined formulas that can be employed with the polyols to form the poly(oxyalkylene)-polyol include 1,2-epoxypropane, 1,2-epoxyethane, 1,2-epoxydocosane, 10,11-epoxydocosane, 2,3-epoxy-4,5-dimethyldodecane, 1,3-epoxypropane, 1,12-epoxydodecane, 1,12-epoxy-2,11-dibutyldodecane, 1,4-epoxy-2-(2,2-diimethyltetradecyl)-butane, and the like.

Transesterification catalysts useful for the transesterification of the mixture of alkyl mercaptocarboxylate and dialkyl thiodicarboxylate and dialkyl polythiodicarboxylate with poly(oxyalkylene)-polyols include those of formula VIII

$$M(OR''')_4 \qquad (VIII)$$

wherein R''' is an alkyl group having from 1 to 10 carbon atoms and M is titanium or zirconium. It is presently preferred to employ tetraalkyl titanates of formula VIII wherein M is titanium and the R''' groups contain from 3 to 8 carbon atoms per group.

Mixtures of alkyl mercaptocarboxylates, dialkyl thiodicarboxylates, and dialkyl dithiodicarboxylates, if any, prepared in accordance with this invention will generally contain from 50 to 95 weight percent alkyl mercaptocarboxylate. However, it is preferred to employ mixtures containing from 55 to 75 weight percent alkyl mercaptocarboxylate.

In order to improve the efficiency of the transesterification reaction, it is frequently desirable to exclude materials which are detrimental to the reaction. For example, water which is useful in the production of the mixed esters is detrimental to the transesterification reaction and can be excluded by means well known in the art such as by purging the mixed esters with a dry inert gas or azeotrope distillation. Water can be removed from the poly(oxyalkylene)-polyol prior to use by purging with a dry, inert gas at an elevated temperature. Alternatively, the mixed ester-polyol mixture can be purged with a dry inert gas, preferably at an elevated temperature before adding the transesterification catalyst.

It is currently convenient to run the transesterification reaction in the absence of diluent. However, if desired, inert diluents may be employed. Sucn diluents include the well-known saturated aliphatic, saturated cycloaliphatic or aromatic hydrocarbons containing from 5 to 8 carbon atoms such as pentane, hexane, isooctane, cyclohexane, benzene, toluene and the xylenes; as well as the well-known acyclic or cyclic ethers containing from 4 to 8 carbon atoms such as diethyl ether, di-n-butyl ether, tetrahydrofuran and p-dioxane; as well as mixtures thereof.

In the transesterification step, it is convenient to employ the mixed esters (alkyl mercaptocarboxylate, dialkyl thiodicarboxylate and dialkyl polythiosdicarboxylate, if any,) and poly(oxyalkylene)-polyol in amounts ranging from 0.8 to 1.2 equivalents of ester group in the mixed esters per equivalent of hydroxy group in the poly)oxyakylene)-polyol, preferably from 1.0 to 1.1, more preferably 1.04 to 1.07, equivalents of ester per equivalent of hydroxy. The transesterification catalyst is generally employed in an amount ranging from 0.1 to 4 and preferably 0.2 to 2 grams of catalyst per gram equivalent of hydroxy groups in the poly(oxyalkylene)-polyol.

The transesterification reaction to produce the poly-(oxyalkylene)-polyester-poly(monosulfide)-polythiol and poly(oxyalkylene)-polyester-poly(monosulfide)-poly(disulfide)-polythiol of this invention is normally carried out at a temperature in the range of 125° to 235° C. and preferably from 165° to 225° C. for a time period in the range of 0.5 to 72 hours and preferably from 6 to 30 hours. The pressure under which the transesterification reaction occurs can be whatever is convenient depending on temperature and volatility of reaction components such as from subatmospheric to superatmospheric. For example, reaction pressures can range from 0.1 to 100 atmospheres, but those from 1 atmosphere to 10 atmospheres are preferred.

Conditions of temperature and pressure are chosen to provide for the continuous removal overhead of R'OH during the course of the transesterification. One skilled in the art will recognize that the continuous removal of a lower alcohol from a transesterification reaction system provides the driving force for the transesterification to occur to a high degree. If, however, one desires a lower degree of transesterification, e.g., the equilibrium value, then removal of the alcohol overhead will not be necessary.

At the completion of the transesterification reaction as evidenced by the cessation of evolution of R'OH, the poly(oxyakylene)-polyester-poly(monosulfide)-polythiol or poly(oxyalkylene)-polyester-poly(monosulfide)-poly(disulfide)-polythiol will generally require no further treatment or working prior to use if no diluent has been used. If, however, further purification or treatment of the product is desired, then well-known procedures such as washing, solvent extraction, etc., may be employed to provide product with the desired degree of purity.

The poly(oxyalkylene-polyester-poly(monosulfide)-polythiol and poly(oxyalkylene)-polyester-poly(-monosulfide)-poly(disulfide)-polythiol prepared according to this invention can be used immediately after preparation or can be stored for a period of time prior to use. They are useful in a variety of sealant and coating formulations such as those described fully in U.S. Pat. Nos. 3,803,089, 3,817,936, 3,829,526, 3,843,381, 3,857,876, 3,919,067 and 3,931,078, the disclosures of which are hereby incorporated by reference.

EXAMPLE I

The following run (Run 1) illustrates the preparation of methyl 3-mercaptopropionate dimethyl thiodipropionate and dimethyl dithiodipropionate and the preparation of a poly(oxyakylene)-polyester-poly(monosulfide)-poly(disulfide)-polythiol therefrom.

Into a one-gallon stainless steel reactor fitted with a stirrer, pressure gauge, temperature measuring device and internal cooling coil was placed methanol (600 ml), concentrated ammonium hydroxide (28 weight percent $NH_3$, 21.6 gm), sulfur (12 gm) and hydrogen sulfide (816 gm). Methyl acrylate (1376 gm) was introduced into the stirred reactor over a 45 minute interval. Over the reaction period the temperature of the reaction mixture increased from 23° C. to 53° C. while the pressure decreased from 1650 kPa to 1150 kPa. After an additional 30 minute period of stirring the reactor was vented to release excess hydrogen sulfide and the remaining reaction solution was transferred to a fractionation apparatus.

A total of 5 runs were made as described above. The resulting reaction mixtures were combined prior to fractional distillation.

A fraction (5889 gm) was collected over a boiling range of 87°–93° C. at 50 torr pressure which contained 98.6 weight percent methyl 3-mercaptopropionate (analyzed by GLC, i.e., gas-liquid chromatography). The undistilled pot residue (3005 gm) contained 85 weight percent dimethyl thiodipropionate and 15 weight percent dimethyl dithiodipropionate (analyzed by GLC).

Into a 3-liter, stirred, heated glass reactor was added polyether polyol (550 gm of LHT-34 from Union Carbide -derived from 1,2,6-hexanetriol and propylene oxide, having a molecular weight of about 4500 and a hydroxyl number of about 34 which is milliequivalents of OH groups per gram of polyol). Nitrogen (0.056 $m^3$/hr) was bubbled through the stirred reactor contents maintained at 100° C. for one hour to remove residual water. The nitrogen flow was then reduced to 0.0056 m³/hr), a reflux condenser was attached and methyl mercaptopropionate (25.9 gm fraction described above), sulfide-disulfide mixture (14.1 gm—undistilled pot residue described above), and tetrabutyl titanate (0.2 ml, du Pont's Tyzor TBT, essentially 0.2 g pure tetrabutyl titanate) were added to the reactor. The stirred reaction mixture was maintained at 177° C. for 24 hours. The nitrogen flow through the reaction mixture swept out the methanol formed in the transesterification reaction. At the end of the 24 hour period, the reflux condenser was removed and the nitrogen flow rate was increased to 0.056 m³/hr with the temperature maintained at 177° C. for one hour to remove volatiles. The resultant poly(oxyalkylene)-polyester-poly(-monosulfide)-poly(disulfide)-polythiol possessed 0.88 weight percent mercaptan sulfur and a viscosity of 6800 centipoises at 25° C.

EXAMPLE II

The following run (Run 2) illustrates preparation of a poly(oxyalkylene)-polyester-poly(monosulfide)-poly(-disulfide)-polythiol employing a methyl mercaptopropionate/dimethyl thiodipropionate/dimethyl dithiodipropionate mixture which was not fractionated after its preparation as was that in Example I.

Methanol, ammonium hydroxide, sulfur and hydrogen sulfide in the same amounts, using the same reactor and the same charging procedure as in Example I were employed. Methyl acrylate (1376 gm) was added to the stirred reactor over a 30 to 40 minute period. Following the methyl acrylate addition and an additional 15 minute stirring period the reaction solutions of 6 successive runs were combined and the methanol was distilled. The remaining reaction product containing methyl mercaptopropionate, dimethyl thiodipropionate and dimethyl dithiodipropionate in a 67.3/27.8/4.9 weight ratio, respectively, (by GLC) was filtered prior to use in the transesterification reaction.

The transesterification reaction was conducted in a stirred, heated reactor. Polyether polyol (29.5 kg LHT-34) was dried as in Example I. The reflux condenser was attached to the reactor and the nitrogen flow was reduced to 0.006 m³/hr prior to addition of the mercaptan-sulfide-disulfide mixture (2083 gm) prepared above and 10.7 ml (10.6 g) tetrabutyl titanate. After the stirred reaction mixture had been maintained at 177° C. for 24 hours the volatiles were stripped as in Example I. The resultant poly(oxyalkylene)- polyester-poly(monosulfide)-poly(disulfide)-polythiol possessed 0.83 weight percent mercaptan sulfur and a viscosity of 6600 centipoises at 25° C.

EXAMPLE III

The following runs (Runs 3 and 4) were conducted as described in Example I except that 0.19 g tetraisopropyl titanate (Run 3) and 0.19 g tetraoctyl titanate (Run 4) were employed as transesterification catalysts. The polymer resulting from Run 3 had 0.90 weight percent mercaptan sulfur and a viscosity of 4800 centipoises at 25° C. The Run 4 polymer had 0.90 weight percent mercaptan sulfur and 4800 centipoises viscosity at 25° C.

EXAMPLE IV

The following runs illustrate the use of the polymers prepared in Runs 1 through 4 in sealant formulations.

The formulation employed in these runs is given in the following recipe:

| Recipe | Parts by Weight |
|---|---|
| Sealant Formulation | |
| Polymer | 20 |
| Chlorinated paraffin[1] | 3 |
| Calcium carbonate | 10 |
| Titanium dioxide | 2 |
| Fumed silica | 1.2 |
| Stabilizer[2] | 0.2 |
| Carbon black | 0.12 |
| Yellow pigment | 0.15 |
| Iron oxide | 0.5 |
| Curing Agent | |
| Dibutyl phthalate | 0.6 |
| Lead dioxide | 0.6 |
| Water | 0.45 |

[1]Chlorafin 50 from Monsanto, a light yellow, viscous oil.
[2]2,2'-methylenebis(4-methyl-6-t-butylphenol).

After the above sealant formulation was prepared, the curing agent components were added and the resulting sealant was heated at 70° C. for 16 hours. Table I gives properties of the resultant cured sealants.

TABLE I

| Run No. | 5 | 6 | 7 | 8 |
|---|---|---|---|---|
| Polymer run no. | 1 | 2 | 3 | 4 |
| 50% Modulus, psi[1] | 44.3 | 32.5 | 30.5 | 27 |
| Tensile Strength | 162.5 | 126.5 | 113 | 106.5 |
| Elongation, % | 680 | >675 | >700 | >700 |

[1]ASTM D 888-56T.

The results in Table I demonstrate that useful sealants were obtained based on the poly(oxyalkylene)-polyester-poly(monosulfide)-poly(disulfide)-polythiols prepared according to the practice of this invention.

EXAMPLE V

Poly(oxyalkylene)-polyester-poly(monosulfide)-poly(disulfide)-polythiol made in accordance with this invention and similar polymer made by reacting a mercaptoalkanoic acid and a thiodialkanoic acid with a poly(oxyalkylene)-polyol and neutralized as disclosed in said U.S. Pat. No. 3,817,936 were subjected to storage conditions in air at room temperature for 60 days. The polymer made in accordance with the invention was stable without the introduction of stabilizers as evidenced by essentially no change in viscosity after 60 days whereas the polymer made from the acids exhibited a two to threefold increase in viscosity after 60 days. As a specific example, control polymer having an initial viscosity of about 7,000 centipoises at 25° C. had a viscosity of greater than 25,000 centipoises at 25° C. after 100 days, the increase in viscosity beginning almost immediately after contact with air. This shows the polymer of the invention is characterized by undergoing no significant viscosity change on storage for 60 days in air at room temperature, whereas the control polymer was essentially unusable.

EXAMPLE VI

Numerous runs were carried out preparing polymer in accordance with this invention using a glass-lined vessel for the transesterification of the type used in the preparation of the control polymer of Example V, the preparation of the control polymer not being possible in stainless steel equipment. Stainless steel coupons Type 304 and 316 were placed in this transesterification vessel during the preparation of the invention polymers and after 700 hours they showed no visible sign of corrosion. The control polymer could not be prepared in contact with stainless steel because of corrosion.

EXAMPLE VII

The following pilot plant run (Run 9) was carried out under essentially the same conditions as Example II except scaled up to larger quantities.

Into a 500 gallon glass-lined reactor was placed 300 lbs. of methanol and 13½ lbs. of concentrated ammonium hydroxide (28 weight percent NH₃) along with 7½ lbs. of sulfur and about 80 gals, of hydrogen sulfide. Then 108 gals. of methyl acrylate was introduced into the reactor over a 2 hour interval. Over the reaction period the temperature of the reaction mixture increased from 29° C. to about 48° C. while the pressure decreased from about 2100 kPa to about 1150 kPa. After an additional 1 hour reaction time the reactor was vented to release excess hydrogen sulfide after which the top of the reactor was connected with a reflux condenser and the reactor heated to a temperature of about 162° C. to drive off water and methanol. It was then cooled down and the resulting product comprising mixed esters of methyl 3-mercaptopropionate, dimethyl thiodipropionate and dimethyl dithiodipropionate were placed in holding drums.

About 3,082 lbs. of polyether polyol (LHT-34 from Union Carbide derived from 1,2,6-hexanetriol and propylene oxide having a molecular weight of about 4,500 and a hydroxyl number of about 34) was introduced into the reactor and heated to 121° C. with nitrogen purge for 1 hour to strip out water. Then 225 lbs. of the mixed esters was introduced back into the reactor, approximately one-half of this being added prior to the addition of the catalyst and the other one-half after the addition of the catalyst. The catalyst added was 1.12 lb. of tetrabutyl titanate (DPont's Tyzor TBT, essentially pure tetrabutyl titanate). The reactor was heated up and maintained at 177° C. for 24 hours with a slight nitrogen flow to sweep out methanol formed during the transesterification reaction period. At the end of the 24 hour period nitrogen flow was increased with the temperature remaining unchanged so as to strip out unreacted methyl 3-mercaptopropionate. The resulting poly(alkylene)-polyester-poly(monosulfide)-poly(disulfide)-polythiol possessed 0.87 weight percent mercaptan sulfur and a viscosity of 6400 centipoises at 25° C. and an acid number of 0.00. The product was obtained in an amount of 3180 lbs.

EXAMPLE VIII

A series of runs was made in which hydrogen sulfide (816 grams, 24 moles), ammonia (6.0 grams), together with water, methanol, and/or sulfur (when used) were charged to a stirred one-gallon stainless steel autoclave without heating or cooling capacity and methyl acrylate (1376 grams, 16 moles) was pumped into the reactor. The time required for the maximum temperature to be reached and the corresponding pressure drop were recorded. After the acrylate had been charged, small samples were withdrawn periodically for analysis by gas-liquid chromatography (GLC) to determine when the reaction was complete. When the GLC analysis showed no further change in proportions of reactants and products, the unreacted hydrogen sulfide was allowed to flash. The remaining portion of the sample was analyzed by GLC. The data obtained in these runs (based on GLC analysis) are summarized below:

TABLE II

| Run No. | CH₃OH[1] | Sulfur[2] | Water[2] | Time MA Addn.[3] | Time to Temp. Peak[4] | Pressure Drop[5] | Rxn Time[6] | Product Distribution[7] | | |
|---|---|---|---|---|---|---|---|---|---|---|
| | | | | | | | | RSH[3] | RSR[6] | RSSR[8] |
| 10 | 0 | 0 | 0 | 38 | 175 | 320–230 | 185 | 50.7 | 49.3 | 0 |
| 11 | 0 | 0.75 | 0.975 | 51 | 72 | 370–245 | 47 | 51.1 | 43.7 | 5.2 |
| 12 | 9.4 | 0.75 | 0.975 | 44 | 44 | 355–245 | 60 | 66.8 | 29.2 | 4.0 |
| 13 | 18.8 | 0.75 | 0.975 | 38 | 38 | 315–225 | 60 | →72.5 | 23.3 | 4.2 |
| 14 | 37.5 | 0.75 | 0.975 | 60 | 60 | 290–210 | 70 | →73.5 | 22.2 | 4.3 |
| 15 | 18.8 | 0 | 0.975 | 41 | 46 | 305–153 | 60 | 57.0 | 43.0 | 0 |
| 16 | 18.8 | 0.75 | 0 | 43 | 48 | 330–170 | (9) | 65.6 | 30.0 | 4.4 |
| 17 | 18.8 | 0.75 | 0.975 | 53 | 53 | 312–212 | 50 | →71.9 | 23.8 | 4.4 |

[1]Milliliters methanol per gram mole of methyl acrylate.
[2]Grams per gram mole of methyl acrylate.
[3]Time in minutes required for methyl acrylate addition to reactor.
[4]Time in minutes from beginning of methyl acrylate addition to maximum temperature.
[5]Pressure drop in psig from beginning of methyl acrylate addition to temperature peak.
[6]Time in minutes from end of methyl acrylate addition to discharge from reactor and flashing of hydrogen sulfide.
[7]Area percent determined by gas liquid chromatography.

[8]R is 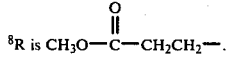
$CH_3O-\overset{O}{\underset{\parallel}{C}}-CH_2CH_2-$.

(9) Allowed to stand overnight at room temperature prior to workup.

EXAMPLE IX

Analyses were conducted to compare the polymer made in accordance with this invention (Example VII) with polymer made in accordance with U.S. Pat. No. 3,817,936. The results are as follows:

TABLE III

| Analytical Test | U.S. 3,817,936 | Invention |
|---|---|---|
| SH, Weight % | 0.74 | 0.84 |
| Total Sulfur, Weight % | 1.3 | 1.3 |
| Number Average Mol. Wt.[1] | 4616 (±243) | 6171 (±318) |
| Carbon, Weight % | 61.0 | 60.7 |
| Hydrogen, Weight % | 10.2 | 10.3 |
| Nitrogen, Weight % | <0.1 | <0.1 |
| Acid Number, mg/g[2] | 0.08 | 0.00 |
| OH Content, meq/g[3] | 0.33 | 0.35 |
| Volatiles at 110 C, 1 Hr., Wt. % | 0.27 | 0.08 |
| Ash, Weight % | 0.065 | 0.011 |
| Composition of Ash | CaSO₄ | [4]TiO₂ |
| Number Average Mol. Wt. ($M_N$)[5] | 8300 | 8300 |
| Weight Average Mol. Wt. ($M_W$)[5] | 26,000 | 24,000 |
| $M_W/M_N$ | 3.2 | 2.9 |

[1]By vapor phase osmometry, VPO, not believed to be accurate at this high molecular weight.
[2]Determined as milligram KOH required to neutralize the acid in one gram of polymer.
[3]Meq of OH per gram of polymer. Determined by reacting with excess acetic anhydride, hydrolyzing and titrating with standard base.
(4)Confirmed by x-ray diffraction.
[5]By gel permeation chromatography - calibrated with polybutadiene.

Differential infrared spectra indicate the polymer produced in accordance with U.S. Pat. No. 3,817,936 has a greater proportion of ether groups to carbonyl groups than does the invention polymer.

As can be seen, the polymer produced in accordance with the invention has no measurable acid number.

While this invention has been described in detail for the purpose of illustration, it is not to be construed as limited thereby but is intended to cover all changes and modifications within the spirit and scope thereof.

I claim:

1. A method for preparing a poly(oxyalkylene)-polyester-poly(sulfide)-polythiol comprising:

(1) reacting hydrogen sulfide with an olefinically unsaturated carboxylate of the formula

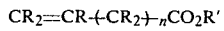

wherein R' is an alkyl radical containing 1 to 5 carbon atoms and R is hyrdogen or R', wherein n is zero or an integer having the value of 1, 2 or 3, and wherein the total number of carbon atoms in all of the R and R' groups is 1 to 15 per molecule;

using an addition catalyst selected from organic and inorganic bases in the presence of a lower alkanol and a cocatalyst consisting essentially of at least one of sulfur and water, wherein the sulfur or water is present in an amount within the range of from 0.0001 to 0.2 part by weight per part by weight unsaturated carboxylate, to produce a mixed ester reaction product;

reacting the thus-obtained mixed ester reaction product in the presence of a transesterification catalyst with a poly(oxyalkylene)-polyol produced by reacting one or more epoxy-substituted hydrocarbons of the formula

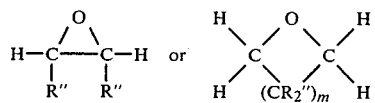

wherein R'' is H or alkyl with the total number of carbon atoms in the molecule being up to 20 and wherein m is an integer of from 1 to 10, with a polyol of the general formula

wherein Y is a hydrocarbon moiety having at least two carbon atoms per moiety and a valence equal to the value of x, x being an integer of at least two.

2. A method according to claim 1 wherein said cocatalyst consists essentially of sulfur and the resulting reaction product with said poly(oxyalkylene)-polyol is a poly(oxyalkylene)-polyester-poly(monosulfide)-poly(disulfide)-polythiol.

3. A method according to claim 1 wherein the ratio of said mixed esters to said poly(oxyalkylene)-polyol is such that there is present from 1.0 to 1.1 equivalents of ester per equivalent of hydroxy group in said poly(oxyalkylene)-polyol.

4. A method according to claim 1 wherein said poly(oxyalkylene)-polyol is produced from 1,2,6-hexanetriol and propylene oxide.

5. A method according to claim 1 wherein said transesterification catalyst is represented by the formula M(OR''')$_4$ wherein R''' is a 1–10 carbon atom alkyl group and M is titanium or zirconium.

6. A method according to claim 1 wherein the cocatalyst consists essentially of both sulfur and water.

7. A method according to claim 6 wherein the sulfur is present in an amount within the range of 0.002 to 0.05 part by weight per part by weight of the unsaturated carboxylate and the water is present in an amount within the range of 0.004 to 0.1 part by weight per part by weight of the unsaturated carboxylate, the lower alkanol is one of methanol, ethanol, and isopropanol, the bases being selected from sodium hydroxide, potassium hydroxide, sodium methoxide, ammonia, ammonium hydroxide, dimethylamine, triethylamine, N,N-diethylaniline, pyridine, and 3-ethyl-4-methylpyridine.

8. A method according to claim 7 wherein the alcohol is present in an amount within the range of 0.04 to 0.4 part by weight per part by weight of the unsaturated carboxylate.

9. A method according to claim 8 wherein the alkanol is methanol.

10. A method according to claim 8 wherein the alkanol is isopropyl alcohol.

11. A method according to claim 10 wherein the hydrogen sulfide is employed in an amount within the range of 1 to 3 moles of hydrogen sulfide per mole of the unsaturated carboxylate.

12. A method according to claim 11 wherein the addition catalyst is ammonium hydroxide.

13. A method according to claim 11 wherein the addition catalyst is triethylamine.

14. A method according to claim 1 wherein the olefinically unsaturated carboxylate is methyl acrylate, the cocatalyst is sulfur and the mixed ester reaction product comprises methyl mercaptopropionate and dialkyl thiodicarboxylate.

15. A method according to claim 14 wherein the transesterification catalyst is tetrabutyl titanate and the poly(oxyalkylene)-polyol is the reaction product of 1,2,6-hexanetriol and propylene oxide.

16. A method according to claim 1 wherein the mixed ester reaction product comprising alkyl mercaptocarboxylate and dialkyl thiodicarboxylate is fractionally distilled to give a fraction enriched in methyl mercaptocarboxylate and the resulting enriched fractions are recombined so as to give a mixed ester reaction product having a predetermined ratio of alkyl mercaptocarboxylate to dialkyl thiodicarboxylate.

17. Poly(oxyalkylene)-polyester-poly(monosulfide)-poly(disulfide)-polythiol characterized by undergoing no significant change in viscosity on storage for 60 days in air at room temperature.

18. Poly(oxyalkylene)-polyester-poly(monosulfide)-poly(disulfide)-polythiol characterized by an acid number of less than 0.01.

19. The composition of claim 18 wherein said acid number is 0.00.

* * * * *